US00PP32733P2

(12) United States Plant Patent
van der Velden

(10) Patent No.: US PP32,733 P2
(45) Date of Patent: Jan. 5, 2021

(54) ***SCHEFFLERA* PLANT NAMED 'OSV001'**

(50) Latin Name: *Schefflera arboricola*
Varietal Denomination: OSV001

(71) Applicant: ForemostCo., Inc., Miami, FL (US)

(72) Inventor: Sjef van der Velden, Sint-Oederode (NL)

(73) Assignee: ForemostCo., Inc., Miami, FL (US)

( * ) Notice: Subject to any disclaimer, the term of this patent is extended or adjusted under 35 U.S.C. 154(b) by 0 days.

(21) Appl. No.: 16/873,303

(22) Filed: Mar. 16, 2020

(51) Int. Cl.
*A01H 5/12* (2018.01)
*A01H 6/00* (2018.01)

(52) U.S. Cl.
USPC ..... Plt./377
CPC ..... *A01H 6/00* (2018.05)

(58) Field of Classification Search
USPC ..... Plt./377
CPC ..... A01H 6/00
See application file for complete search history.

*Primary Examiner* — Anne Marie Grunberg
(74) *Attorney, Agent, or Firm* — The Webb Law Firm

(57) ABSTRACT

A new and distinct *Schefflera* plant having solid green colored leaflets that is suitable for potted plant production.

2 Drawing Sheets

Botanical classification: *Schefflera arboricola.*
Varietal denomination: 'OSV001'.

BACKGROUND OF THE INVENTION

The present invention comprises a new and distinct variety of *Schefflera* plant having the varietal name of 'OSV001'. The new variety was discovered in 2015 in la Guacima, Costa Rica with the purposes of providing *Schefflera* plants with better color, greater stability, and better growing characteristics. The new variety was identified in a cultivated production field as a naturally occurring mutation of *Schefflera* variety named 'Gold Capella' (unpatented). The new variety exhibits similar growth characteristics to 'Gold Capella', but differs from 'Gold Capella' in exhibiting solid green colored leaflets, while 'Gold Capella' has variegated green and yellow-green colored leaflets. Asexual reproductions of the new variety by stem and tip cuttings first occurred in 2015 in Sint-Oedenrode, Netherlands. 'OSV001' has been trial and field tested and has been found to retain its distinctive characteristics and remain true to type through successive propagations. The present invention has not been evaluated under all possible environmental conditions. The phenotype may vary with variations in environment without a change in the genotype of the plant.

When 'OSV001' is compared to *Schefflera* plant named 'OSV002' (U.S. Plant patent application Ser. No. 16/873,304), the varieties differ in leaflet color ('OSV002' has variegated yellow-green and green colored leaflets and 'OSV001' has solid green colored leaflets), overall height ('OSV002' is taller than 'OSV001'), and number of leaves ('OSV002' has more leaves than 'OSV001').

DESCRIPTION OF THE DRAWINGS

The accompanying photographic drawings taken at approximately 24 months of age illustrate the new variety, with the colors being as nearly true as is possible with color illustrations of this type.

DESCRIPTION OF THE PLANT

Figure 1:
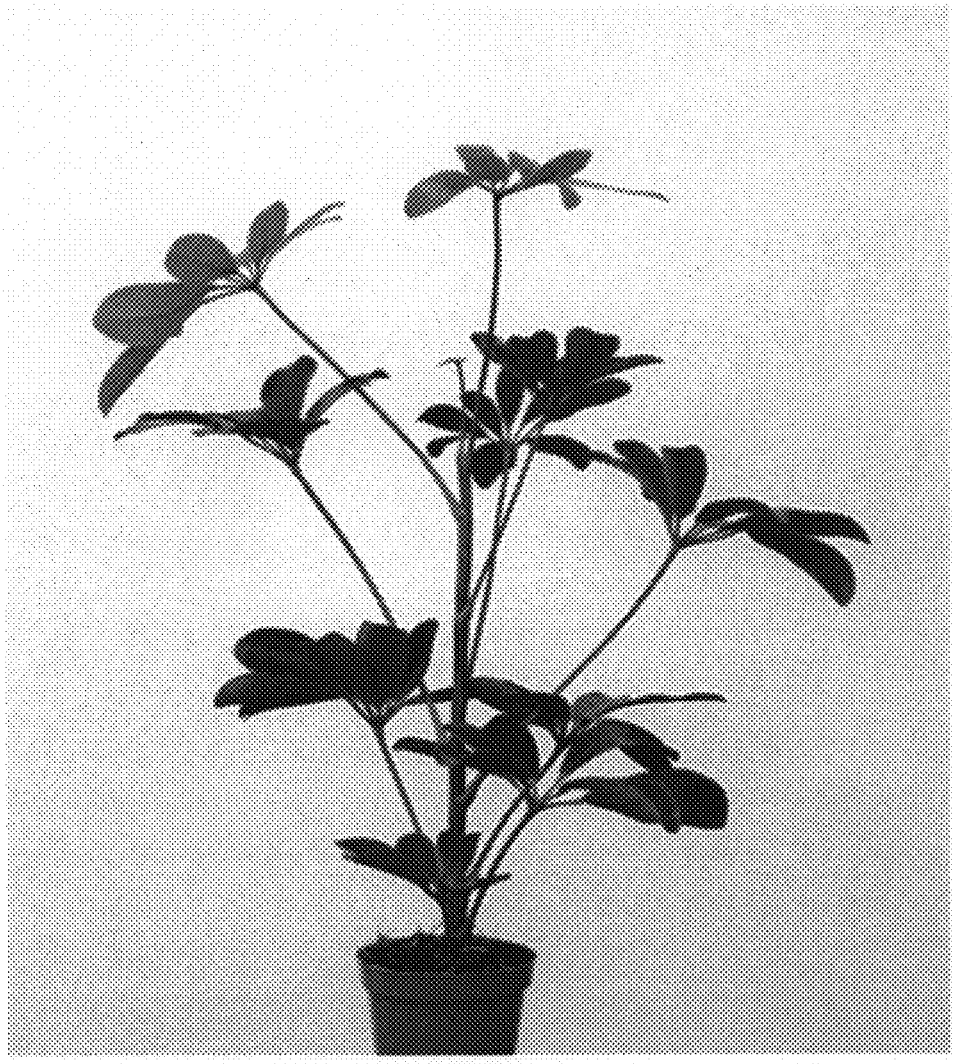
FIG. 1 shows a plant of the new variety.
Figure 2:
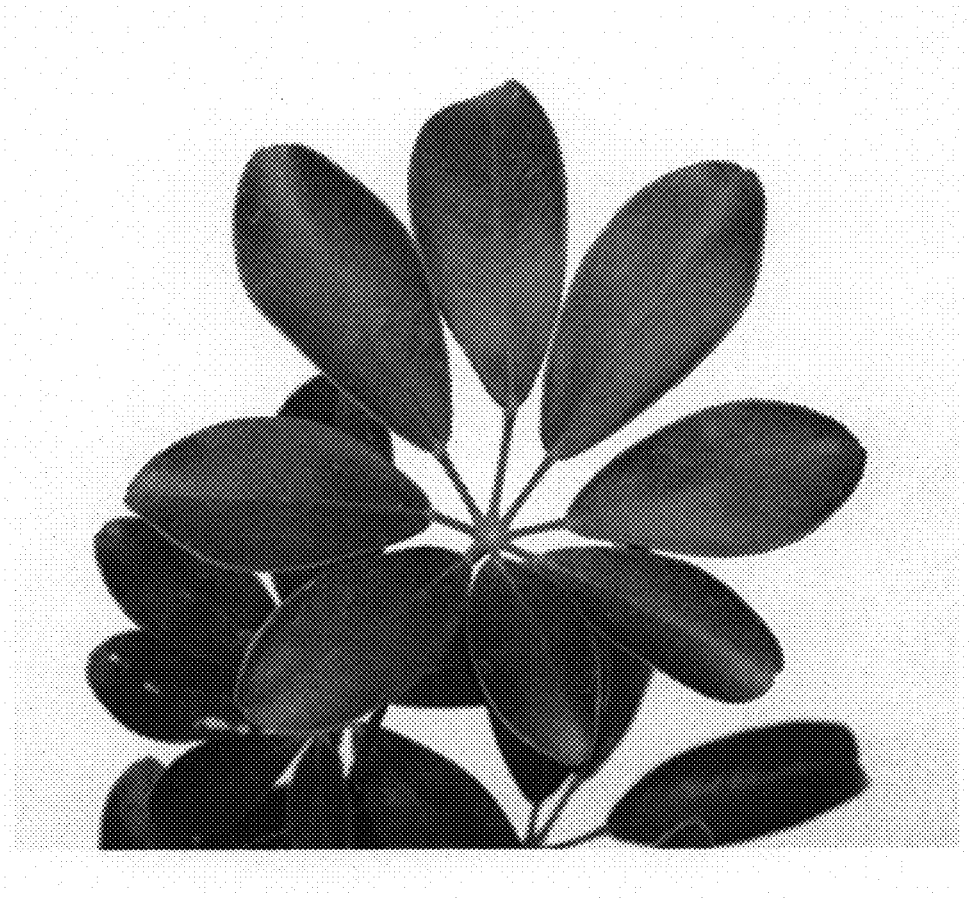
FIG. 2 shows a close-up view of the foliage of the new variety.

The following detailed description sets forth the characteristics of the new variety at approximately 24 months of age. The data which defines these characteristics was collected under natural light in August of 2020 in Sint-Oedenrode, Netherlands. Plants of the new variety were grown in 8.5 cm round pots in a conventional, cold-storage greenhouse in Sint-Oedenrode, Netherlands. Color references are primarily to The 2015 R.H.S. Colour Chart of The Royal Horticultural Society of London, 6$^{th}$ Edition, except where general color terms are used.

PLANT

Type: Perennial and evergreen, suitable for potted plant production.

*Time to produce a finished plant from propagation.*—About 6 months at 20° C.
*Preferred container size.*—8.5 cm or larger pots.
*Overall plant shape.*—Ovate to broadly ovate.
*Growth habit.*—Upright.
*Plant height (soil level to top of foliar plant).*—Average of 36.0 cm.
*Plant diameter.*—Average of 31.7 cm.
*Growth rate.*—Moderate.
*Plant vigor.*—Moderate to high.
*Branching habit.*—Main stem grows from the base with no lateral branching.
*Basal branching.*—Present.
*Pinching required.*—No, but can improve branching.
*Specific disease/pest resistance.*—Nothing unusual noted to date.
*USDA plant hardiness zones.*—From Zone 10 to Zone 13.
*Heat/cold tolerance.*—Range not fully tested, but at least hardy from +4° C. to 40° C.

*Rain tolerance.*—High.

*Wind tolerance.*—Moderate.

Main stem:

*Number.*—Average of 1.

*Length.*—Average of 21.1 cm.

*Diameter.*—Average of 0.8 cm.

*Internode length.*—Average of 3.6 cm.

*Shape.*—Rounded.

*Luster.*—Matte.

*Angle.*—Average of 85° from horizontal.

*Strength.*—Strong.

*Color.*—Developing: Yellow-Green Group RHS 144A. Mature: Yellow-Green Group RHS 146A. At internodes: Yellow-Green Group RHS 146C.

*Pubescence.*—None present.

*Lenticels.*—Presence: On mature stems. Shape: Elliptic. Length: Average of 1.0 mm. Diameter: Average of 0.5 mm. Color: Greyed-Orange Group RHS 164B to 164C.

Leaves:

*Arrangement.*—Alternate and compound.

*Number per plant.*—Average of 8.

*Number of leaflets per leaf.*—Average of 8-40% of the leaves have 9.

*Whole leaf.*—Shape: Orbicular. Aspect: Slightly concave. Length: 14.3 cm. Width: 13.5 cm.

*Petiole.*—Length: Average of 15.7 cm. Diameter: Average of 3.0 mm. Texture: Smooth, glabrous (both sides). Luster: Slightly glossy (both sides). Strength: Strong. Upper side color: Green Group RHS 138B. Under side color: Yellow-Green Group RHS 144B.

*Leaflet.*—Shape: Obovate. Length: Average of 6.2 cm. Width: Average of 3.0 cm. Apex: Emarginate. Base: Obtuse. Margin: Entire, with none to very slightly coarsely undulate. Sheathing: None. Lobing: None. Venation: Pinnate. Upper surface: Texture: Smooth, glabrous. Pubescence: None. Rugosity: None. Luster: Slightly glossy. Young color: Yellow-Green Group RHS 144A. Mature color: In between Green Group RHS NN137A and Yellow-Green Group RHS 147A, but slightly darker and closest to RHS 147A. Venation color: Green Group RHS 143B. Under surface: Texture: Smooth, glabrous. Pubescence: None. Rugosity: None. Luster: Matte. Young color: Yellow-Green Group RHS 147C. Mature color: In between Yellow-Green Group RHS 147B and 148B. Venation color: Yellow-Green Group RHS 144A.

*Petiolule.*—Length: Average of 1.8 cm. Diameter: Average of 1.5 mm. Texture: Smooth, glabrous (both sides). Luster: Slightly glossy (both sides). Strength: Strong. Upper side color: Yellow-Green Group RHS 144A. Under side color: Yellow-Green Group RHS 145B.

Stipules/tendrils/thorns/prickles/flowers/seeds/fruit: None observed.

I claim:

1. A new and distinct variety of *Schefflera* plant, as is herein illustrated and described.

* * * * *